US012636349B2

(12) United States Patent
Witherspoon et al.

(10) Patent No.: US 12,636,349 B2
(45) Date of Patent: May 26, 2026

(54) ANIMAL FEED COMPOSITIONS AND METHODS OF USE

(71) Applicant: Syngenta Participations AG, Basel (CH)

(72) Inventors: David Witherspoon, Minnetonka, MN (US); Tammiraj Kumar Iragavarapu, Minnetonka, MN (US)

(73) Assignee: SYNGENTA CROP PROTECTION AG, Basel (CH)

( * ) Notice: Subject to any disclaimer, the term of this patent is extended or adjusted under 35 U.S.C. 154(b) by 0 days.

(21) Appl. No.: 16/798,733

(22) Filed: Feb. 24, 2020

(65) Prior Publication Data

US 2020/0230215 A1 Jul. 23, 2020

Related U.S. Application Data

(62) Division of application No. 15/562,957, filed as application No. PCT/US2016/026656 on Apr. 8, 2016, now Pat. No. 11,154,594.

(60) Provisional application No. 62/145,587, filed on Apr. 10, 2015.

(51) Int. Cl.

| | |
|---|---|
| ***A23K 50/00*** | (2016.01) |
| ***A23K 10/30*** | (2016.01) |
| ***A23K 20/189*** | (2016.01) |
| ***A23K 50/10*** | (2016.01) |
| ***A23K 50/30*** | (2016.01) |
| ***A23K 50/70*** | (2016.01) |
| ***A23K 50/80*** | (2016.01) |
| ***A61K 9/00*** | (2006.01) |
| ***A61K 36/899*** | (2006.01) |
| ***A61K 38/47*** | (2006.01) |
| ***C12N 9/26*** | (2006.01) |
| ***C12N 9/28*** | (2006.01) |

(52) U.S. Cl.

CPC .............. *A61K 38/47* (2013.01); *A23K 10/30* (2016.05); *A23K 20/189* (2016.05); *A23K 50/10* (2016.05); *A61K 9/0056* (2013.01); *A61K 36/899* (2013.01); *C12N 9/2417* (2013.01); *C12Y 302/01001* (2013.01)

(58) Field of Classification Search

None

See application file for complete search history.

(56) References Cited

U.S. PATENT DOCUMENTS

| | | | |
|---|---|---|---|
| 5,543,576 | A | 8/1996 | van Ooijen et al. |
| 5,714,474 | A | 2/1998 | Van Ooijen et al. |
| 7,033,627 | B2 | 4/2006 | Van Ooyen et al. |
| 7,102,057 | B2 | 9/2006 | Lanahan et al. |
| 7,407,677 | B2 | 8/2008 | Callen et al. |
| 7,557,262 | B2 | 7/2009 | Lanahan et al. |
| 7,635,799 | B2 | 12/2009 | Johnson et al. |
| 7,727,726 | B2 | 6/2010 | Cates et al. |
| 7,781,201 | B2 | 8/2010 | Callen et al. |
| 7,785,855 | B2 | 8/2010 | Callen et al. |
| 7,816,108 | B2 | 10/2010 | Callen et al. |
| 7,855,322 | B2 | 12/2010 | Lanahan et al. |
| 7,914,993 | B2 | 3/2011 | Batie et al. |
| 7,915,020 | B2 | 3/2011 | Cates et al. |
| 7,919,681 | B2 | 4/2011 | Lanahan et al. |
| 8,003,863 | B1 | 8/2011 | Goodwin |
| 8,093,453 | B2 | 1/2012 | Johnson et al. |
| 9,018,447 | B2 | 4/2015 | Lanahan et al. |
| 9,125,357 | B2 | 9/2015 | Dallmier et al. |
| 9,816,119 | B2 | 11/2017 | Aux |
| 10,100,324 | B2 | 10/2018 | Ral et al. |
| 10,196,669 | B2 | 2/2019 | Costello et al. |
| 2003/0135885 | A1 | 7/2003 | Lanahan et al. |
| 2006/0230473 | A1 | 10/2006 | Johnson et al. |
| 2007/0243236 | A1 | 10/2007 | Cerda et al. |
| 2009/0324571 | A1 | 12/2009 | Steinberg et al. |
| 2011/0277044 | A1 | 11/2011 | Pettersson et al. |
| 2014/0234279 | A1 | 8/2014 | Millan |
| 2015/0203860 | A1 | 7/2015 | Lanahan et al. |
| 2017/0101663 | A1 | 4/2017 | Moser et al. |
| 2018/0030491 | A1 | 2/2018 | Aux |

FOREIGN PATENT DOCUMENTS

| | | | |
|---|---|---|---|
| EP | 0449376 | B1 | 5/2001 |
| RU | 2 073 715 | C1 | 2/1997 |
| RU | 2 533 001 | C2 | 11/2014 |
| UA | 10246 | | 12/1996 |
| WO | 2003000905 | A2 | 1/2003 |
| WO | 2003/018766 | A3 | 3/2003 |
| WO | 03/059087 | A1 | 7/2003 |

(Continued)

OTHER PUBLICATIONS

"Novel Food Information" (obtained from https://www.canada.ca/en/health-canada/services/food-nutrition/genetically-modified-foods-other-novel-foods/approved-products/alpha-amylase-corn-event-3272.html; published 2008, 7 pages (Year: 2008).*

(Continued)

*Primary Examiner* — David Steadman

(74) *Attorney, Agent, or Firm* — Karen A. Magri

(57) ABSTRACT

The invention provides an animal feed composition comprising microbial α-amylase. The invention further provides methods of increasing the growth (weight gain), the average daily weight gain or the efficiency of feed utilization by an animal or reducing the number of days needed to achieve a desired weight in an animal, comprising feeding to the animal an animal feed composition of the present invention.

26 Claims, No Drawings

Specification includes a Sequence Listing.

(56) References Cited

FOREIGN PATENT DOCUMENTS

| | | | |
|---|---|---|---|
| WO | 2005096804 | A2 | 10/2005 |
| WO | 2006098952 | A2 | 9/2006 |
| WO | 2009/140504 | A1 | 11/2009 |
| WO | 2010088447 | A1 | 8/2010 |
| WO | 2010091221 | A1 | 8/2010 |
| WO | 2012004759 | A2 | 1/2012 |

OTHER PUBLICATIONS

Kung, L., "Silage Temperatures: How Hot is Too Hot?", Jul. 2011, 2 pages (Year: 2011).*

Benton et al., "Effects of Corn Moisture and Length of Ensiling on Dry Matter Digestibility and Rumen Degradable Protein", 2005 Nebraska Beef Report pp. 31-33, 2005 (Year: 2005).*

Definition of "control", obtained from Dictionary.com on Feb. 26, 2024, 2 pages (Year: 2024).*

Leahy et al., "Effects of treating corn silage with alpha-amylase and (or) sorbic acid on beef cattle growth and carcass characteristics," J. Anim. Sci. (1990), 68: pp. 490-497.

Miller et al., "Effect of altering the physical form of corn silage on utilization by dairy cattle," Journal of Dairy Science, vol. 52, No. 12, pp. 1955-1960, 1969.

Syngenta Seeds, Inc. Alpha-Amylase Maize Event 3272, OECD Unique Identifier SYN-E3272-5, Final Environmental Assessment, Feb. 2011, USDA APHIS.

DD2008-70: Determination of the Safety of Syngenta Seeds Inc.'s Corn (*Zea mays* L. (Linnaeus)) Event 3272, Canadian Food Inspection Agency, Mar. 2008.

Determination of Nonregulated Status for Syngenta Seeds Event 3272 Corn (Alpha-amylase and phosphomannose isomerase corn), Animal and Plant Health Inspection Service, U.S. Department of Agriculture, Feb. 11, 2011.

National Environmental Policy Act Decision and Finding of No Significant Impact; Syngenta Seeds, Inc.; Alpha-Amylase Maize Event 3272; USDA, APHIS Biotechnology Regulatory Services dated Feb. 11, 2011.

Meale et al., "Board-Invited Review: Opportunities and challenges in using exogenous enzymes to improve ruminant production," Journal of Animal Science (2014), vol. 92: pp. 427-442.

International Search Report mailed Oct. 26, 2016 in Application No. PCT/US16/26656.

Supplementary European Search Report for EP16777361.3, mailed on Mar. 14, 2019.

Hu et al., "Short communication: In vitro ruminal fermentability of a modified corn cultivar expressing a thermotolerant a-amylase," J. Dairy Sci., 93:4846-4849 (2010).

Schoonmaker et al., "Effect of feeding corn modified to contain a unique amylase on performance and carcass characteristics of feedlot steers," The Professional Animal Scientist 30 (2014) 561-565.

Response to APHIS/BRS Review for Technical Completeness of Syngenta's petition for a Determination of Non-regulated Status for Corn Event 3272, assigned APHIS No. 05-280-01p (Jan. 10, 2007).

Robert Plamondon, "Save money on chicken feed," Mother Earth News (Jul. 29, 2019).

Tricarico et al., "Effects of a dietary Aspergillus oryzae extract containing—amylase activity on performance and carcass characteristics of finishing beef cattle," Journal of Animal Science (Mar. 2007).

"99% of Domestic Feed Corn is GMO," Yonhap News, May 13, 2010, 02 Pages, Retrieved from the Internet: URL: https://www.yna.co.kr/view/AKR20100512218800017?section=popup/print, with Machine Translation.

Application for import and use of genetically modified Event 3272 maize under Regulation (EC) No. 1829/2003, Retrieved from URL: https://euginius.eu/euginius/api/literature/pdf/2170524150539240096, published 2013, 28 Pages (Year: 2013).

EFSA: "Scientific Opinion," European Food Safety Authority Journal, Aug. 21, 2013, vol. 11:3252, pp. 01-27.

Zinn R.A., et al., "Flaking Corn: Processing Mechanics, Quality Standards, and Impacts on Energy Availability and Performance of Feedlot Cattle," Journal of Animal Science, 2002, vol. 80, pp. 1145-1156 (13 Pages).

* cited by examiner

SEQUENCE LISTING

```
<160> NUMBER OF SEQ ID NOS: 5

<210> SEQ ID NO 1
<211> LENGTH: 436
<212> TYPE: PRT
<213> ORGANISM: Artificial
<220> FEATURE:
<223> OTHER INFORMATION: Synthetic

<400> SEQUENCE: 1

Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Ser Gly Gly Tyr Ser Met Gly Tyr Asp
    50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
```

```
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Ala Ala Phe
                245                 250                 255

Asp Asn Lys Asn Ile Pro Ala Leu Val Glu Ala Leu Lys Asn Gly Gly
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Ser Ile Val Tyr Tyr Asp Ser Asp Glu Met
            340                 345                 350

Ile Phe Val Arg Asn Gly Tyr Gly Ser Lys Pro Gly Leu Ile Thr Tyr
        355                 360                 365

Ile Asn Leu Gly Ser Ser Lys Val Gly Arg Trp Val Tyr Val Pro Lys
    370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
            420                 425                 430

Cys Gly Val Gly
        435
```

<210> SEQ ID NO 2
<211> LENGTH: 1308
<212> TYPE: DNA
<213> ORGANISM: Artificial
<220> FEATURE:
<223> OTHER INFORMATION: Synthetic

<400> SEQUENCE: 2

```
atggccaagt acctggagct ggaggagggc ggcgtgatca tgcaggcgtt ctactgggac      60

gtcccgagcg gaggcatctg gtgggacacc atccgccaga agatccccga gtggtacgac     120

gccggcatct ccgcgatctg gataccgcca gcttccaagg gcatgtccgg gggctactcg     180

atgggctacg acccgtacga ctacttcgac ctcggcgagt actaccagaa gggcacggtg     240

gagacgcgct tcgggtccaa gcaggagctc atcaacatga tcaacacggc gcacgcctac     300

ggcatcaagg tcatcgcgga catcgtgatc aaccacaggg ccggcggcga cctggagtgg     360

aacccgttcg tcggcgacta cacctggacg gacttctcca aggtcgcctc cggcaagtac     420

accgccaact acctcgactt ccaccccaac gagctgcacg cgggcgactc cggcacgttc     480
```

ggcggctacc cggacatctg ccacgacaag tcctgggacc agtactggct ctgggcctcg 540
caggagtcct acgcggccta cctgcgctcc atcggcatcg acgcgtggcg cttcgactac 600
gtcaagggct acggggcctg ggtggtcaag gactggctca actggtgggg cggctgggcg 660
gtgggcgagt actgggacac caacgtcgac gcgctgctca actgggccta ctcctccggc 720
gccaaggtgt tcgacttccc cctgtactac aagatggacg cggccttcga caacaagaac 780
atcccggcgc tcgtcgaggc cctgaagaac ggcggcacgg tggtctcccg cgacccgttc 840
aaggccgtga ccttcgtcgc caaccacgac acggacatca tctggaacaa gtacccggcg 900
tacgccttca tcctcaccta cgagggccag cccacgatct tctaccgcga ctacgaggag 960
tggctgaaca aggacaagct caagaacctg atctggattc acgacaacct cgcgggcggc 1020
tccactagta tcgtgtacta cgactccgac gagatgatct tcgtccgcaa cggctacggc 1080
tccaagcccg gcctgatcac gtacatcaac ctgggctcct ccaaggtggg ccgctgggtg 1140
tacgtcccga agttcgccgg cgcgtgcatc cacgagtaca ccggcaacct cggcggctgg 1200
gtggacaagt acgtgtactc ctccggctgg gtctacctgg aggccccggc ctacgacccc 1260
gccaacggcc agtacggcta ctccgtgtgg tcctactgcg gcgtcggc 1308

<210> SEQ ID NO 3
<211> LENGTH: 2223
<212> TYPE: DNA
<213> ORGANISM: Artificial
<220> FEATURE:
<223> OTHER INFORMATION: Synthetic

<400> SEQUENCE: 3
atggccaagt acctggagct ggaggagggc ggcgtgatca tgcaggcgtt ctactgggac 60
gtcccgagcg gaggcatctg gtgggacacc atccgccaga agatccccga gtggtacgac 120
gccggcatct ccgcgatctg gataccgcca gcttccaagg gcatgtccgg gggctactcg 180
atgggctacg acccgtacga ctacttcgac ctcggcgagt actaccagaa gggcacggtg 240
gagacgcgct tcgggtccaa gcaggagctc atcaacatga tcaacacggc gcacgcctac 300
ggcatcaagg tcatcgcgga catcgtgatc aaccacaggg ccggcggcga cctggagtgg 360
aacccgttcg tcggcgacta cacctggacg gacttctcca aggtcgcctc cggcaagtac 420
accgccaact acctcgactt ccaccccaac gagctgcacg cgggcgactc cggcacgttc 480
ggcggctacc cggacatctg ccacgacaag tcctgggacc agtactggct ctgggcctcg 540
caggagtcct acgcggccta cctgcgctcc atcggcatcg acgcgtggcg cttcgactac 600
gtcaagggct acggggcctg ggtggtcaag gactggctca actggtgggg cggctgggcg 660
gtgggcgagt actgggacac caacgtcgac gcgctgctca actgggccta ctcctccggc 720
gccaaggtgt tcgacttccc cctgtactac aagatggacg cggccttcga caacaagaac 780
atcccggcgc tcgtcgaggc cctgaagaac ggcggcacgg tggtctcccg cgacccgttc 840
aaggccgtga ccttcgtcgc caaccacgac acggacatca tctggaacaa gtacccggcg 900
tacgccttca tcctcaccta cgagggccag cccacgatct tctaccgcga ctacgaggag 960
tggctgaaca aggacaagct caagaacctg atctggattc acgacaacct cgcgggcggc 1020
tccactagta tcgtgtacta cgactccgac gagatgatct tcgtccgcaa cggctacggc 1080
tccaagcccg gcctgatcac gtacatcaac ctgggctcct ccaaggtggg ccgctgggtg 1140
tacgtcccga agttcgccgg cgcgtgcatc cacgagtaca ccggcaacct cggcggctgg 1200
gtggacaagt acgtgtactc ctccggctgg gtctacctgg aggccccggc ctacgacccc 1260

```
gccaacggcc agtacggcta ctccgtgtgg tcctactgcg gcgtcggcac atcgattgct   1320
ggcatcctcg aggccgacag ggtcctcacc gtcagcccct actacgccga ggagctcatc   1380
tccggcatcg ccaggggctg cgagctcgac aacatcatgc gcctcaccgg catcaccggc   1440
atcgtcaacg gcatggacgt cagcgagtgg gaccccagca gggacaagta catcgccgtg   1500
aagtacgacg tgtcgacggc cgtggaggcc aaggcgctga acaaggaggc gctgcaggcg   1560
gaggtcgggc tcccggtgga ccggaacatc ccgctggtgg cgttcatcgg caggctggaa   1620
gagcagaagg gccccgacgt catggcggcc gccatcccgc agctcatgga gatggtggag   1680
gacgtgcaga tcgttctgct gggcacgggc aagaagaagt tcgagcgcat gctcatgagc   1740
gccgaggaga agttcccagg caaggtgcgc gccgtggtca agttcaacgc ggcgctggcg   1800
caccacatca tggccggcgc cgacgtgctc gccgtcacca gccgcttcga gccctgcggc   1860
ctcatccagc tgcaggggat gcgatacgga acgccctgcg cctgcgcgtc caccggtgga   1920
ctcgtcgaca ccatcatcga aggcaagacc gggttccaca tgggccgcct cagcgtcgac   1980
tgcaacgtcg tggagccggc ggacgtcaag aaggtggcca ccaccttgca gcgcgccatc   2040
aaggtggtcg gcacgccggc gtacgaggag atggtgagga actgcatgat ccaggatctc   2100
tcctggaagg gccctgccaa gaactgggag aacgtgctgc tcagcctcgg ggtcgccggc   2160
ggcgagccag gggttgaagg cgaggagatc gcgccgctcg ccaaggagaa cgtggccgcg   2220
ccc                                                                  2223
```

```
<210> SEQ ID NO 4
<211> LENGTH: 3285
<212> TYPE: DNA
<213> ORGANISM: Aspergillus shirousami

<400> SEQUENCE: 4

gccaccccgg ccgactggcg ctcccagtcc atctacttcc tcctcaccga ccgcttcgcc     60
cgcaccgacg gctccaccac cgccacctgc aacaccgccg accagaagta ctgcggcggc    120
acctggcagg gcatcatcga caagctcgac tacatccagg gcatgggctt caccgccatc    180
tggatcaccc cggtgaccgc ccagctcccg cagaccaccg cctacggcga cgcctaccac    240
ggctactggc agcaggacat ctactccctc aacgagaact acggcaccgc cgacgacctc    300
aaggccctct cctccgccct ccacgagcgc ggcatgtacc tcatggtgga cgtggtggcc    360
aaccacatgg gctacgacgg cgccggctcc tccgtggact actccgtgtt caagccgttc    420
tcctcccagg actacttcca cccgttctgc ttcatccaga actacgagga ccagacccag    480
gtggaggact gctggctcgg cgacaacacc gtgtccctcc cggacctcga caccaccaag    540
gacgtggtga agaacgagtg gtacgactgg gtgggctccc tcgtgtccaa ctactccatc    600
gacggcctcc gcatcgacac cgtgaagcac gtgcagaagg acttctggcc cgggctacaac    660
aaggccgccg gcgtgtactg catcggcgag gtgctcgacg tggacccggc ctacacctgc    720
ccgtaccaga acgtgatgga cggcgtgctc aactacccga tctactaccc gctcctcaac    780
gccttcaagt ccacctccgg ctcgatggac gacctctaca acatgatcaa caccgtgaag    840
tccgactgcc cggactccac cctcctcggc accttcgtgg agaaccacga caacccgcgc    900
ttcgcctcct acaccaacga catcgccctc gccaagaacg tggccgcctt catcatcctc    960
aacgacggca tcccgatcat ctacgccggc caggagcagc actacgccgg cggcaacgac   1020
ccggccaacc gcgaggccac ctggctctcc ggctacccga ccgactccga gctgtacaag   1080
```

```
ctcatcgcct ccgccaacgc catccgcaac tacgccatct ccaaggacac cggcttcgtg   1140

acctacaaga actggccgat ctacaaggac gacaccacca tcgccatgcg caagggcacc   1200

gacggctccc agatcgtgac catcctctcc aacaagggcg cctccggcga ctcctacacc   1260

ctctccctct ccggcgccgg ctacaccgcc ggccagcagc tcaccgaggt gatcggctgc   1320

accaccgtga ccgtgggctc cgacggcaac gtgccggtgc cgatggccgg cggcctcccg   1380

cgcgtgctct acccgaccga gaagctcgcc ggctccaaga tatgctcctc ctccaagccg   1440

gccaccctcg actcctggct ctccaacgag gccaccgtgg cccgcaccgc catcctcaac   1500

aacatcggcg ccgacggcgc ctgggtgtcc ggcgccgact ccggcatcgt ggtggcctcc   1560

ccgtccaccg acaacccgga ctacttctac acctggaccc gcgactccgg catcgtgctc   1620

aagaccctcg tggacctctt ccgcaacggc gacaccgacc tcctctccac catcgagcac   1680

tacatctcct cccaggccat catccagggc gtgtccaacc cgtccggcga cctctcctcc   1740

ggcggcctcg gcgagccgaa gttcaacgtg gacgagaccg cctacgccgg ctcctggggc   1800

cgcccgcagc gcgacggccc ggccctccgc gccaccgcca tgatcggctt cggccagtgg   1860

ctcctcgaca acggctacac ctccgccgcc accgagatcg tgtggccgct cgtgcgcaac   1920

gacctctcct acgtggccca gtactggaac cagaccggct acgacctctg ggaggaggtg   1980

aacggctcct ccttcttcac catcgccgtg cagcaccgcg ccctcgtgga gggctccgcc   2040

ttcgccaccg ccgtgggctc ctcctgctcc tggtgcgact cccaggcccc gcagatcctc   2100

tgctacctcc agtccttctg gaccggctcc tacatcctcg ccaacttcga ctcctcccgc   2160

tccggcaagg acaccaacac cctcctcggc tccatccaca ccttcgaccc ggaggccggc   2220

tgcgacgact ccaccttcca gccgtgctcc ccgcgcgccc tcgccaacca caaggaggtg   2280

gtggactcct tccgctccat ctacaccctc aacgacggcc tctccgactc cgaggccgtg   2340

gccgtgggcc gctacccgga ggactcctac tacaacggca acccgtggtt cctctgcacc   2400

ctcgccgccg ccgagcagct ctacgacgcc ctctaccagt gggacaagca gggctccctg   2460

gagatcaccg acgtgtccct cgacttcttc aaggccctct actccggcgc cgccaccggc   2520

acctactcct cctcctcctc cacctactcc tccatcgtgt ccgccgtgaa gaccttcgcc   2580

gacggcttcg tgtccatcgt ggagacccac gccgcctcca acggctccct ctccgagcag   2640

ttcgacaagt ccgacggcga cgagctgtcc gcccgcgacc tcacctggtc ctacgccgcc   2700

ctcctcaccg ccaacaaccg ccgcaactcc gtggtgccgc cgtcctgggg cgagacctcc   2760

gcctcctccg tgccgggcac ctgcgccgcc acctccgcct ccggcaccta ctcctccgtg   2820

accgtgacct cctggccgtc catcgtggcc accggcggca ccaccaccac cgccaccacc   2880

accggctccg gcggcgtgac ctccacctcc aagaccacca ccaccgcctc caagacctcc   2940

accaccacct cctccacctc ctgcaccacc ccgaccgccg tggccgtgac cttcgacctc   3000

accgccacca ccacctacgg cgagaacatc tacctcgtgg gctccatctc ccagctcggc   3060

gactgggaga cctccgacgg catcgccctc tccgccgaca agtacacctc ctccaacccg   3120

ccgtggtacg tgaccgtgac cctcccggcc ggcgagtcct tcgagtacaa gttcatccgc   3180

gtggagtccg acgactccgt ggagtgggag tccgacccga accgcgagta caccgtgccg   3240

caggcctgcg gcgagtccac cgccaccgtg accgacacct ggcgc                   3285
```

<210> SEQ ID NO 5
<211> LENGTH: 1320
<212> TYPE: DNA
<213> ORGANISM: Artificial

-continued

```
<220> FEATURE:
<223> OTHER INFORMATION: Synthetic

<400> SEQUENCE: 5

atggcgaagc acttggctgc catgtgctgg tgcagcctcc tagtgcttgt actgctctgc     60

ttgggctccc agctggccca atcccaggtc ctcttccagg ggttcaactg ggagtcgtgg    120

aagaagcaag gtgggtggta caactacctc ctggggcggg tggacgacat cgccgcgacg    180

ggggccacgc acgtctggct cccgcagccg tcgcactcgg tggcgccgca ggggtacatg    240

cccggccggc tctacgacct ggacgcgtcc aagtacggca cccacgcgga gctcaagtcg    300

ctcaccgcgg cgttccacgc caagggcgtc cagtgcgtcg ccgacgtcgt gatcaaccac    360

cgctgcgccg actacaagga cggccgcggc atctactgcg tcttcgaggg cggcacgccc    420

gacagccgcc tcgactgggg ccccgacatg atctgcagcg acgacacgca gtactccaac    480

gggcgcgggc accgcgacac gggggccgac ttcgccgccg cgcccgacat cgaccacctc    540

aacccgcgcg tgcagcagga gctctcggac tggctcaact ggctcaagtc cgacctcggc    600

ttcgacggct ggcgcctcga cttcgccaag ggctactccg ccgccgtcgc caaggtgtac    660

gtcgacagca ccgcccccac cttcgtcgtc gccgagatat ggagctccct ccactacgac    720

ggcaacggcg agccgtccag caaccaggac gccgacaggc aggagctggt caactgggcg    780

caggcggtgg gcggccccgc cgcggcgttc gacttcacca ccaagggcgt gctgcaggcg    840

gccgtccagg gcgagctgtg gcgcatgaag gacggcaacg gcaaggcgcc cgggatgatc    900

ggctggctgc cggagaaggc cgtcacgttc gtcgacaacc acgacaccgg ctccacgcag    960

aactcgtggc cattcccctc cgacaaggtc atgcagggct acgcctatat cctcacgcac   1020

ccaggaactc catgcatctt ctacgaccac gttttcgact ggaacctgaa gcaggagatc   1080

agcgcgctgt ctgcggtgag gtcaagaaac gggatccacc cggggagcga gctgaacatc   1140

ctcgccgccg acggggatct ctacgtcgcc aagattgacg acaaggtcat cgtgaagatc   1200

gggtcacggt acgacgtcgg gaacctgatc ccctcagact tccacgccgt tgcccctggc   1260

aacaactact gcgtttggga gaagcacggt ctgagagttc cagcggggcg gcaccactag   1320
```

ANIMAL FEED COMPOSITIONS AND METHODS OF USE

RELATED APPLICATION INFORMATION

This application is a divisional of co-pending U.S. application Ser. No. 15/562,957, which claims priority under 35 U.S.C. § 371 from International Application No. PCT/US2016/026656, filed 8 Apr. 2016, which claims the benefit of U.S. Provisional Application No. 62/145,587, filed 10 Apr. 2015, the contents of which applications are all incorporated by reference herein in their entirety.

STATEMENT REGARDING ELECTRONIC SUBMISSION OF A SEQUENCE LISTING

A Sequence Listing in ASCII text format, submitted under 37 C.F.R. § 1.821, entitled "80783-WO-REG-ORG_P-1_ST25.txt", 22,000 bytes in size, generated on Sep. 28, 2017 and filed via EFS-Web is provided in lieu of a paper copy. This Sequence Listing is hereby incorporated by reference into the specification for its disclosures.

FIELD OF THE INVENTION

The present invention relates to animal feed compositions and methods of using the same for increasing weight gain in animals

BACKGROUND OF THE INVENTION

Animal feeds can be classified into two groups: (1) concentrates or compound feeds and (2) roughages. Concentrates or compound feeds are high in energy value, including fat, cereal grains and their by-products (barley, corn, oats, rye, wheat), high-protein oil meals or cakes (soybean, canola, cottonseed, peanut and the like), and by-products from processing of sugar beets, sugarcane, animals, and fish, which can be produced in the form of pellets or crumbles. Concentrates or compound feeds can be complete in that they can provide all the daily required food needs or they can provide a part of the ration, supplementing whatever else may be provided as a food ration. Roughage includes pasture grasses, hays, silage, root crops, straw, and stover (cornstalks).

Feed constitutes the largest cost of raising animals for food production. Thus, the present invention is directed to compositions and methods for improving the efficiency of animal feed utilization, thereby reducing the cost of production.

SUMMARY OF THE INVENTION

One aspect of the present invention provides an animal feed composition comprising microbial α-amylase. In some aspects, the microbial α-amylase comprises a polypeptide having at least about 80% identity to the amino acid sequence of SEQ ID NO:1 or a polypeptide encoded by a nucleotide sequence having at least about 80% identity to the nucleotide sequence of SEQ ID NO:2, SEQ ID NO:3, SEQ ID NO:4 and/or SEQ ID NO:5.

Another aspect of the present invention provides an animal feed composition comprising plant material, wherein the plant material comprises an expressed heterologous α-amylase. In some particular embodiments, the expressed heterologous α-amylase is encoded by a nucleotide sequence having at least about 80% identity to the nucleotide sequence of SEQ ID NO:2, SEQ ID NO:3, SEQ ID NO:4 and/or SEQ ID NO:5 or comprises a polypeptide having at least about 80% identity to the amino acid sequence of SEQ ID NO:1.

The present invention further provides an animal feed composition comprising plant material from a transgenic plant or plant part comprising a recombinant α-amylase encoded by a nucleotide sequence having at least about 80% identity to the nucleotide sequence of SEQ ID NO:2, SEQ ID NO:3, SEQ ID NO:4 and/or SEQ ID NO:5 or comprising a polypeptide having at least about 80% identity to the amino acid sequence of SEQ ID NO:1.

In other aspects, the present invention provides a corn ration comprising plant material from a transgenic corn plant or plant part stably transformed with a recombinant α-amylase encoded by a nucleotide sequence having at least about 80% identity to the nucleotide sequence of SEQ ID NO:2 , SEQ ID NO:3, SEQ ID NO:4 and/or SEQ ID NO:5. Additional aspects of the invention provide an animal feed composition comprising the corn ration of the invention.

A further aspect of the invention provides a method of increasing the average daily weight gain of an animal, comprising feeding to said animal an animal feed composition of the present invention, wherein the average daily weight gain of the animal is increased by about 0.05 lbs/day to about 10 lbs/day.

An additional aspect of the invention provides a method of increasing the growth rate (weight gain) of an animal, comprising feeding to said animal an animal feed composition of the present invention, wherein the growth rate of the animal is increased by about 0.05 lb/day to about 10 lbs/day.

A still further aspect of the invention provides a method for reducing the number of days needed to achieve a desired weight in an animal, comprising feeding to said animal an animal feed composition of the present invention, thereby reducing the number of days needed to achieve a desired weight.

In other aspects, a method of increasing the efficiency of feed utilization by an animal is provided, the method comprising feeding to said animal an animal feed composition of the present invention in an amount effective to increase the efficiency of feed utilization by said animal The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DETAILED DESCRIPTION OF THE INVENTION

Unless the context indicates otherwise, it is specifically intended that the various features of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage, an amount or a time period and the like, is meant to encompass variations of ±20%, ±10%, ±5%, ±1%, ±0.5%, or even ±0.1% of the specified amount (e.g., an amount of weight gained or feed provided).

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The present invention is directed to compositions and methods for improving the efficiency of animal feed utilization, thereby reducing the cost of production. The present inventors have made the surprising discovery that animals fed an animal feed composition comprising microbial α-amylase can have an increase in the average daily weight gain or growth rate, an increase in the efficiency of feed utilization or require a reduced number of days to achieve a desired weight as compared to animals not fed said feed composition.

Accordingly, in one aspect of the invention, an animal feed composition comprising microbial α-amylase is provided. In further aspects of the invention, the microbial α-amylase comprises a polypeptide having at least 80% identity to the amino acid sequence of SEQ ID NO:1 or a polypeptide encoded by a nucleotide sequence having at least 80% identity to the nucleotide sequence of SEQ ID NO:2, SEQ ID NO:3, SEQ ID NO:4 and/or SEQ ID NO:5. In some embodiments, the α-amylase is a liquid. Thus, in some embodiments of the invention, an animal feed composition of the invention can be a supplement that comprises a liquid microbial α-amylase that can be added to the feed provided to an animal.

In another aspect, the present invention provides an animal feed composition comprising plant material, wherein the plant material comprises an expressed recombinant α-amylase. In some particular embodiments, the expressed recombinant α-amylase is encoded by a nucleotide sequence having at least about 80% identity to the nucleotide sequence of SEQ ID NO:2, SEQ ID NO:3, SEQ ID NO:4 and/or SEQ ID NO:5 or comprises a polypeptide having at least about 80% identity to the amino acid sequence of SEQ ID NO:1. Thus, in further embodiments, the invention provides an animal feed composition comprising plant material from a transgenic plant or plant part comprising a recombinant α-amylase encoded by a nucleotide sequence having at least about 80% identity to the nucleotide sequence of SEQ ID NO:2, SEQ ID NO:3, SEQ ID NO:4 and/or SEQ ID NO:5 or comprising a polypeptide having at least about 80% identity to the amino acid sequence of SEQ ID NO:1.

In particular embodiments, the transgenic plant or plant part can comprise about 1% to about 100% by weight of the plant material. Thus, for example, the transgenic plant or plant part can comprise about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% by weight of the plant material, and the like, or any range therein. Thus, in some embodiments, the plant material can comprise one or more different types of plants. Thus, for example, the plant material can be from a plant in which recombinant or heterologous (e.g., microbial) α-amylase is expressed. In other embodiments, the plant material comprises, consists essentially of, or consists of material from a plant in which recombinant or heterologous (e.g., microbial) α-amylase is expressed and material from a plant not expressing said recombinant or heterologous α-amylase (e.g., a commodity plant). Thus, in some embodiments, when the plant material comprises material from a plant in which recombinant or heterologous (e.g., microbial) α-amylase is expressed and material from a plant not expressing said recombinant or heterologous α-amylase (e.g., a commodity plant), the material from a plant in which recombinant or heterologous (e.g., microbial) α-amylase is expressed can comprise from about 1% to about 99% by weight of the plant material and the material from a plant not expressing said recombinant or heterologous α-amylase can comprise from about 99% to about 1% by weight of the plant material.

In further embodiments, plant material can comprise from about 5% to about 100% by weight of the animal feed composition. Thus, for example, the plant material can comprise about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% by weight of the animal feed composition, and the like, and/or any range therein.

The animal feed of the invention can be in any form that is useful with this invention. Thus, in some embodiments, the form of the animal feed can be, but is not limited to, pellets, grain including one or more types of grain mixed (i.e., mixed grain), a mixture of grain and pellets, silage, dry-rolled, steam flaked, whole kernel, coarsely cracked kernels (e.g., coarsely cracked corn), high moisture corn and/or any combination thereof. In some embodiments, the animal feed can comprise other components, including but not limited to coarsely cracked kernels, wet distillers grain, dry distillers grain, corn silage, supplements/liquid supplements, corn gluten feed, and/or ground hay.

As used herein, the term "plant material" includes any plant part, including but not limited to endosperm, embryos (germ), pericarp (bran coat), pedicle (tip cap), pollen, ovules, seeds (grain), leaves, flowers, branches, stems, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. Further, as used herein, "plant cell" refers to a structural and physiological unit of the plant, which comprises a cell wall and also may refer to a protoplast. A plant cell of the invention can be in the form of an isolated single cell or can be a cultured cell or can be a part of a higher-organized unit such as, for example, a plant tissue or a plant organ. A "protoplast" is an isolated plant cell without a cell wall or with only parts of the cell wall. Thus, in some embodiments of the invention, a transgenic plant or plant part comprising a recombinant α-amylase encoded by a nucleotide sequence of the invention comprises a cell comprising said recombinant α-amylase encoded by a nucleotide sequence of the invention, wherein the cell is a cell of any plant or plant part including, but not limited to, a root cell, a leaf cell, a tissue culture cell, a seed cell, a flower cell, a fruit cell, a pollen cell, and the like. In representative embodiments, the plant material can he a seed or grain.

The plant material can be from any plant. In some embodiments, the plant material is from a plant in which recombinant or heterologous (e.g., microbial) α-amylase can be expressed. Further, as discussed herein, in other embodiments, the plant material can be a mixture of plant material from a plant in which recombinant or heterologous (e.g., microbial) α-amylase is expressed and from a plant not expressing said recombinant or heterologous α-amylase (e.g., a commodity plant). Thus, in representative embodiments, the plant material can be a mixture of normal "commodity" plant material (e.g., commodity corn) and plant material from a transgenic plant of the present invention expressing recombinant or heterologous α-amylase.

Thus, in some embodiments, the plant material can be from a corn plant, a sorghum plant, a wheat plant, a barley plant, a rye plant, an oat plant, a rice plant, and/or a millet plant. In representative embodiments, the plant material can be from a corn plant. In other embodiments, the plant material can be a seed or grain from a corn plant. In particular embodiments, the plant material can be a corn plant comprising corn event 3272 (see, U.S. Pat. No. 8,093,453).

In some embodiment, the invention provides a "total mixed ration" comprising plant material from a transgenic corn plant or plant part stably transformed with a recombinant α-amylase encoded by a nucleotide sequence having about 80% identity to the nucleotide sequence of SEQ ID NO:2, SEQ ID NO:3, SEQ ID NO:4 and/or SEQ ID NO:5 or comprising a polypeptide having at least about 80% identity to the amino acid sequence of SEQ ID NO:1. As used herein, "total mixed ration" can mean the 24 hour feed allowance for an individual animal that includes, for example, plant material from a transgenic corn plant or plant part (e.g., corn kernels, coarsely cracked corn, and the like), supplements and additives, (e.g., vitamins and minerals), and/or "roughages" (e.g., pasture grasses, hays, silage, root crops, straw, and stover (cornstalks)).

In some embodiments, the plant material from the transgenic corn plant or plant part comprises from about 1% to about 100% by weight of the total mixed ration. Thus, for example, the transgenic plant or plant part can comprise about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% by weight of the plant material, and the like, and/or any range therein.

In other embodiments, an animal feed composition is provided that comprises a total mixed ration of the invention. In some embodiments, the total mixed ration can comprise about 5% to about 100% by weight of the animal feed composition. Thus, for example, the total mixed ration can comprise about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% by weight of the animal feed composition, and the like, and/or any range therein. In representative embodiments, the total mixed ration comprises about 50% of the animal feed composition.

In still further embodiments, the invention provides a corn ration comprising plant material from a transgenic corn plant or plant part stably transformed with a recombinant α-amylase encoded by a nucleotide sequence having about 80% identity to the nucleotide sequence of SEQ ID NO:2, SEQ ID NO:3, SEQ ID NO:4 and/or SEQ ID NO:5 or comprising a polypeptide having at least about 80% identity to the amino acid sequence of SEQ ID NO:1. As used herein, "corn ration" means the 24 hour corn allowance for an individual animal.

In some embodiments, the plant material from the transgenic corn plant or plant part comprises from about 1% to about 100% by weight of the corn ration. Thus, for example, the transgenic plant or plant part can comprise about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% by weight of the plant material, and the like, and/or any range therein.

In other embodiments, an animal feed composition is provided that comprises a corn ration of the invention. In some embodiments, the corn ration can comprise about 5% to about 100% by weight of the animal feed composition. Thus, for example, the corn ration can comprise about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% by weight of the animal feed composition, and the like, and/or any range therein. In representative embodiments, the corn ration comprises about 50% of the animal feed composition.

In some embodiments, the total mixed ration can comprise wet corn gluten feed that can be about 10% to about 40% by weight of the animal feed composition. In further embodiments the total mixed ration can comprise wet corn gluten feed that can be about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, by weight of the animal feed composition.

In other embodiments, the total mixed ration can comprise modified distillers grains with solubles that can be about 5% to about 25% by weight of the animal feed composition. In further embodiments the total mixed ration can comprise modified distillers grains with solubles that can be about 5%, 6%, 7%, 8%, 9%, 10%, 11%, 12%, 13%, 14%, 15%, 16%, 17%, 18%, 19%, 20%, 21%, 22%, 23%, 24%, 25%, by weight of the animal feed composition.

In further embodiments, the total mixed ration can comprise wet distillers grains with solubles that can be about 5% to about 25% by weight of the animal feed composition. In further embodiments the total mixed ration can comprise wet distillers grains with solubles that can be about 5%, 6%, 7%, 8%, 9%, 10%, 11%, 12%, 13%, 14%, 15%, 16%, 17%, 18%, 19%, 20%, 21%, 22%, 23%, 24%, 25%, by weight of the animal feed composition.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention (e.g., SEQ ID NO:1, SEQ ID NO:2, SEQ ID NO:3, SEQ ID NO:4, SEQ ID NO:5). "Orthologous," as used herein, refers to homologous nucleotide sequences and/or amino acid sequences in different species that arose from a common ancestral gene during speciation. A homologue of this invention has a significant sequence identity (e.g., 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to SEQ ID NO:1, SEQ ID NO:2, SEQ ID NO:3, SEQ ID NO:4 or SEQ ID NO:5.

A homologue of SEQ ID NO:1, SEQ ID NO:2, SEQ ID NO:3, SEQ ID NO:4 and/or SEQ ID NO:5 can be utilized with any feed composition or method of the invention, alone or in combination with one another and/or with SEQ ID NO:1, SEQ ID NO:2, SEQ ID NO:3, SEQ ID NO:4 and/or SEQ ID NO:5.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

The phrase "substantially identical," in the context of two nucleic acid molecules, nucleotide sequences or protein sequences, refers to two or more sequences or subsequences that have at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 95%, at least about 96%, at least about 97%, at least about 98%, or at least about 99% nucleotide or amino acid residue identity, when compared and aligned for maximum correspondence, as measured using one of the following sequence comparison algorithms, described herein and as known in the art, or by visual inspection. In some embodiments of the invention, the substantial identity exists over a region of the sequences that is at least about 50 residues to about 200 residues, about 50 residues to about 150 residues, and the like, in length. Thus, in some embodiments of the invention, the substantial identity exists over a region of the sequences that is at least about 50, about 60, about 70, about 80, about 90, about 100, about 110, about 120, about 130, about 140, about 150, about 160, about 170, about 180, about 190 , about 200, or more residues in length. In a further embodiment, the sequences are substantially identical over the entire length of the coding regions. Furthermore, in representative embodiments, substantially identical nucleotide or protein sequences perform substantially the same function (e.g., α-amylase activity). Thus, in some particular embodiments, the sequences are substantially identical over at least about 150 residues and have α-amylase activity.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially identical when the two sequences hybridize to each other under stringent conditions. In some representative embodiments, two nucleotide sequences considered to be substantially identical hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point (Tm) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleotide sequences which have more than 100 complementary residues on a filter in a Southern or Northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide In general, a signal to noise ratio of 2× or higher than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences (e.g., SEQ ID NO:2, SEQ ID NO:3, SEQ ID NO:4, SEQ ID NO:5). In one embodiment, a reference nucleotide sequence hybridizes to the "test" nucleotide sequence in 7% sodium dodecyl sulfate (SDS), 0.5 M $NaPO_4$, 1 mM EDTA at 50° C. with washing in 2×SSC, 0.1% SDS at 50° C. In another embodiment, the reference nucleotide sequence hybridizes to the "test"

nucleotide sequence in 7% sodium dodecyl sulfate (SDS), 0.5 M $NaPO_4$, 1 mM EDTA at 50° C. with washing in 1x SSC, 0.1% SDS at 50° C. or in 7% sodium dodecyl sulfate (SDS), 0.5 M $NaPO_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M $NaPO_4$, 1 mM EDTA at 50° C. with washing in 0.1×SSC, 0.1% SDS at 50° C., or in 7% sodium dodecyl sulfate (SDS), 0.5 M $NaPO_4$, 1 mM EDTA at 50° C. with washing in 0.1×SSC, 0.1% SDS at 65° C.

In particular embodiments, a further indication that two nucleotide sequences or two polypeptide sequences are substantially identical can be that the protein encoded by the first nucleic acid is immunologically cross reactive with, or specifically binds to, the protein encoded by the second nucleic acid. Thus, in some embodiments, a polypeptide can be substantially identical to a second polypeptide, for example, where the two polypeptides differ only by conservative substitutions.

Accordingly, in some embodiments of the invention, nucleotide sequences having significant sequence identity to the nucleotide sequence of SEQ ID NO:2, SEQ ID NO:3, SEQ ID NO:4 and/or SEQ ID NO:5 are provided. "Significant sequence identity" or "significant sequence similarity" means at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100% identity or similarity with another nucleotide sequence. Thus, in additional embodiments, "significant sequence identity" or "significant sequence similarity" means a range of about 70% to about 100%, about 75% to about 100%, about 80% to about 100%, about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, and/or about 99% to about 100% identity or similarity with another nucleotide sequence. Therefore, in some embodiments, a nucleotide sequence of the invention is a nucleotide sequence that has significant sequence identity to the nucleotide sequence of SEQ ID NO:2, SEQ ID NO:3, SEQ ID NO:4 or SEQ ID NO:5 and encodes a polypeptide having α-amylase activity. In some embodiments, a nucleotide sequence of the invention is a nucleotide sequence that has 80% to 100% identity to the nucleotide sequence of SEQ ID NO:2, SEQ ID NO:3, SEQ ID NO:4 or SEQ ID NO:5 and encodes a polypeptide having α-amylase activity. In representative embodiments, a nucleotide sequence of the invention is a nucleotide sequence that has 95% identity to the nucleotide sequence of SEQ ID NO:2, SEQ ID NO:3, SEQ ID NO:4 or SEQ ID NO:5and encodes a polypeptide having α-amylase activity.

In some embodiments, a polypeptide of the invention comprises, consists essentially of, or consists of an amino acid sequence that is at least 70% identical, e.g., at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100% identical to the amino acid sequence of SEQ ID NO:1 and has a amylase activity.

In some embodiments, a polypeptide or nucleotide sequence can be a conservatively modified variant. As used herein, "conservatively modified variant" refer to polypeptide and nucleotide sequences containing individual substitutions, deletions or additions that alter, add or delete a single amino acid or nucleotide or a small percentage of amino acids or nucleotides in the sequence, where the alteration results in the substitution of an amino acid with a chemically similar amino acid. Conservative substitution tables providing functionally similar amino acids are well known in the art.

As used herein, a conservatively modified variant of a polypeptide is biologically active and therefore possesses the desired activity of the reference polypeptide (e.g., α-amylase activity) as described herein. The variant can result from, for example, a genetic polymorphism or human manipulation. A biologically active variant of the reference polypeptide can have at least about 40%, 45%, 50%, 55%, 60%, 65%, 70%, 75%, 80%, 85%, 90%, 91%, 92%, 93%, 94%, 95%, 96%, 97%, 98%, 99%, or more sequence identity or similarity (e.g., about 40% to about 99% or more sequence identity or similarity and any range therein) to the amino acid sequence for the reference polypeptide as determined by sequence alignment programs and parameters described elsewhere herein. An active variant can differ from the reference polypeptide sequence by as few as 1-15 amino acid residues, as few as 1-10, such as 6-10, as few as 5, as few as 4, 3, 2, or even 1 amino acid residue.

Naturally occurring variants may exist within a population. Such variants can be identified by using well-known molecular biology techniques, such as the polymerase chain reaction (PCR), and hybridization as described below. Synthetically derived nucleotide sequences, for example, sequences generated by site-directed mutagenesis or PCR-mediated mutagenesis which encode a polypeptide of the invention, are also included as variants. One or more nucleotide or amino acid substitutions, additions, or deletions can be introduced into a nucleotide or amino acid sequence disclosed herein, such that the substitutions, additions, or deletions are introduced into the encoded protein. The additions (insertions) or deletions (truncations) may be made at the N-terminal or C-terminal end of the native protein, or at one or more sites in the native protein. Similarly, a substitution of one or more nucleotides or amino acids may be made at one or more sites in the native protein.

For example, conservative amino acid substitutions may be made at one or more predicted preferably nonessential amino acid residues. A "nonessential" amino acid residue is a residue that can be altered from the wild-type sequence of a protein without altering the biological activity, whereas an "essential" amino acid is required for biological activity. A "conservative amino acid substitution" is one in which the amino acid residue is replaced with an amino acid residue with a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, where such residues are essential for protein activity.

For example, amino acid sequence variants of the reference polypeptide can be prepared by mutating the nucleotide sequence encoding the enzyme. The resulting mutants can be expressed recombinantly in plants, and screened for those that retain biological activity by assaying for α-amylase activity using methods well known in the art. Methods for mutagenesis and nucleotide sequence alterations are known in the art. See, e.g., Kunkel (1985) *Proc. Natl. Acad. Sci. USA* 82:488-492; Kunkel et al. (1987) *Methods in Enzymol.* 154:367-382; and *Techniques in Molecular Biology* (Walker & Gaastra eds., MacMillan Publishing Co. 1983) and the references cited therein; as well as U.S. Pat. No. 4,873,192. Clearly, the mutations made in the DNA encoding the variant must not disrupt the reading frame and preferably will not create complimentary regions that could produce secondary mRNA structure. See, EP Patent Application Publication No. 75,444. Guidance as to appropriate amino acid substitutions that do not affect biological activity of the protein of interest may be found in the model of Dayhoff et al. (1978) *Atlas of Protein Sequence and Structure* (National Biomedical Research Foundation, Washington, D.C.), herein incorporated by reference.

The deletions, insertions and substitutions in the polypeptides described herein are not expected to produce radical changes in the characteristics of the polypeptide (e.g., the activity of the polypeptide). However, when it is difficult to predict the exact effect of the substitution, deletion or insertion in advance of doing so, one of skill in the art will appreciate that the effect can be evaluated by routine screening assays that can screen for the particular polypeptide activities of interest (e.g., α-amylase activity).

In some embodiments, the compositions of the invention can comprise active fragments of the polypeptide. As used herein, "fragment" means a portion of the reference polypeptide that retains the polypeptide activity of α-amylase. A fragment also means a portion of a nucleic acid molecule encoding the reference polypeptide. An active fragment of the polypeptide can be prepared, for example, by isolating a portion of a polypeptide-encoding nucleic acid molecule that expresses the encoded fragment of the polypeptide (e.g., by recombinant expression in vitro), and assessing the activity of the fragment. Nucleic acid molecules encoding such fragments can be at least about 150, 200, 250, 300, 350, 400, 450, 500, 550, 600, 650, 700, 800, 900, 1000, 1100, 1200, 1300, 1400, 1500, 1600, 1700, 1800, 1900, 2000, 2100, or 2200 contiguous nucleotides, or any range therein, or up to the number of nucleotides present in a full-length polypeptide-encoding nucleic acid molecule. As such, polypeptide fragments can be at least about 50, 60, 70, 80, 90, 100, 125, 150, 175, 200, 225, 250, 275, 300, 325, 350, 375, 400, 425, 450, 475, 500, 525, 550, 525, 550, 600, 625, 650, 675, or 700 contiguous amino acid residues, or any range therein, or up to the total number of amino acid residues present in the full-length polypeptide. Thus, in some embodiments, the invention provides a polypeptide comprising, consisting essentially of, or consisting of at least about 150 contiguous amino acid residues of a polypeptide of the invention (e.g., SEQ ID NO:1) and having α-amylase activity.

As used herein, the terms "express," "expresses," "expressed" or "expression," and the like, with respect to a nucleic acid molecule and/or a nucleotide sequence (e.g., RNA or DNA) indicates that the nucleic acid molecule and/or nucleotide sequence is transcribed and, optionally, translated. Thus, a nucleic acid molecule and/or nucleotide sequence may express or produce a polypeptide of interest or a functional untranslated RNA.

A "heterologous" or "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid sequence is a nucleotide sequence naturally associated with a host cell into which it is introduced.

Also as used herein, the terms "nucleic acid," "nucleic acid molecule," "nucleotide sequence" and "polynucleotide" can be used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

In some embodiments, the recombinant nucleic acids molecules, nucleotide sequences and polypeptides of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In other embodiments, an isolated nucleic acid molecule, nucleotide sequence or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the recombinant nucleic acid molecules, nucleotide sequences and their encoded polypeptides are "isolated" in that, by the hand of man, they exist apart from their native environment and therefore are not products of nature, however, in some embodiments, they can be introduced into and exist in a recombinant host cell.

In some embodiments, the nucleotide sequences and/or nucleic acid molecules of the invention can be operatively associated with a variety of promoters for expression in host cells (e.g., plant cells). As used herein, "operatively associated with," when referring to a first nucleic acid sequence that is operatively linked to a second nucleic acid sequence, means a situation when the first nucleic acid sequence is placed in a functional relationship with the second nucleic acid sequence. For instance, a promoter is operatively associated with a coding sequence if the promoter effects the transcription or expression of the coding sequence.

A DNA "promoter" is an untranslated DNA sequence upstream of a coding region that contains the binding site for RNA polymerase and initiates transcription of the DNA. A "promoter region" can also include other elements that act as regulators of gene expression. Promoters can include, for example, constitutive, inducible, temporally regulated, developmentally regulated, chemically regulated, tissue-preferred and tissue-specific promoters for use in the preparation of recombinant nucleic acid molecules, i.e., chimeric genes. In particular aspects, a "promoter" useful with the invention is a promoter capable of initiating transcription of a nucleotide sequence in a cell of a plant.

A "chimeric gene" is a recombinant nucleic acid molecule in which a promoter or other regulatory nucleotide sequence is operatively associated with a nucleotide sequence that codes for an mRNA or which is expressed as a protein, such that the regulatory nucleotide sequence is able to regulate transcription or expression of the associated nucleotide sequence. The regulatory nucleotide sequence of the chimeric gene is not normally operatively linked to the associated nucleotide sequence as found in nature.

The choice of promoter will vary depending on the temporal and spatial requirements for expression, and also depending on the host cell to be transformed. Thus, for example, expression of a nucleotide sequence can be in any plant and/or plant part, (e.g., in leaves, in stalks or stems, in ears, in inflorescences (e.g., spikes, panicles, cobs, etc.), in roots, seeds and/or seedlings, and the like). Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Promoters useful with the invention include, but are not limited to, those that drive expression of a nucleotide sequence constitutively, those that drive expression when induced, and those that drive expression in a tissue—or developmentally-specific manner. These various types of promoters are known in the art.

Examples of constitutive promoters include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. Further, the promoter expression cassettes described by McElroy et al. (*Mol. Gen. Genet.* 231: 150-160 (1991)) can be easily modified for the expression of nucleotide sequences and are particularly suitable for use in monocotyledonous hosts.

In some embodiments, tissue specific/tissue preferred promoters can be used. Tissue specific or preferred expression patterns include, but are not limited to, green tissue specific or preferred, root specific or preferred, stem specific or preferred, and flower specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as (3-conglycinin, cruciferin, napin and phaseolin), zein (e.g., gamma zein) or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of nucleotide sequences in plants, particularly maize, include but are not limited to those that direct expression in root, pith, leaf or pollen. Such promoters are disclosed, for example, in PCT Publication WO 93/07278, herein incorporated by reference in its entirety. Other non-limiting examples of tissue specific or tissue preferred promoters include the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; and the cestrum yellow leaf curling virus promoter disclosed in PCT Publication WO 01/73087, all incorporated by reference herein.

Additional examples of tissue-specific/tissue preferred promoters include, but are not limited to, the root-specific promoters RCc3 (Jeong et al. *Plant Physiol.* 153:185-197 (2010)) and RB7 (U.S. Pat. No. 5459252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenowyl-L-methionine synthetase (SAMS) (Vander Mijnsbrugge et al. (1996) *Plant and Cell Physiology,* 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: Genetic Engineering of Plants (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) Nature 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Particularly useful for seed-specific expression is the pea vicilin promoter (Czako et al. (1992) *Mol. Gen. Genet.* 235:33-40; as well as the seed-specific promoters disclosed in U.S. Pat. ent No. 5,625,136. In some embodiments, the promoter can be an endosperm-specific promoter including but not limited to a maize gamma-zein promoter or a maize ADP-gpp promoter.

Useful promoters for expression in mature leaves are those that are switched on at the onset of senescence, such as the SAG promoter from *Arabidopsis* (Gan et al. (1995) *Science* 270:1986-1988).

In addition, promoters functional in plastids can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used. Thus, for example, chemical-regulated promoters can be used to modulate the expression of a gene in a plant through the application of an exogenous chemical regulator. Regulation of the expression of nucleotide sequences via promoters that are chemically regulated enables the polypeptides of the invention to be synthesized only when the crop plants are treated with the inducing chemicals. Depending upon the objective, the promoter may be a chemical-inducible promoter, where application of a chemical induces gene expression, or a chemical-repressible promoter, where application of the chemical represses gene expression.

Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid (e.g., the PR1a system), steroid steroid-responsive promoters (see, e.g., the glucocorticoid-inducible promoter in Schena et al. (1991) *Proc. Natl. Acad. Sci. USA* 88, 10421-10425 and McNellis et al. (1998) *Plant J.* 14, 247-257) and tetracycline-inducible and tetracycline-repressible promoters (see, e.g., Gatz et al. (1991) *Mol. Gen. Genet.* 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) *Plant J.* 11:605-612), and ecdysone-inducible system promoters.

Other non-limiting examples of inducible promoters include ABA—and turgor-inducible romoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), and the glyceraldehyde-3-phosphate dehydrogenase promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one can use any of the inducible promoters described in Gatz (1996) *Current Opinion Biotechnol.* 7:168-172 and Gatz (1997) *Annu. Rev. Plant Physiol. Plant Mol. Biol.* 48:89-108. Other chemically inducible promoters useful for directing the expression of the nucleotide sequences of this invention in plants are disclosed in U.S. Pat. No. 5,614,395 herein incorporated by reference in its entirety. Chemical induction of gene expression is also detailed in the published application EP 0 332 104 (to Ciba-Geigy) and U.S. Pat. No. 5,614,395. In some embodiments, a promoter for chemical induction can be the tobacco PR-1a promoter.

A polypeptide of this invention may or may not be targeted to a compartment within the plant through use of a signal sequence. Numerous signal sequences are known to influence the expression or targeting of a polynucleotide to a particular compartment/tissue or outside a particular compartment/tissue. Suitable signal sequences and targeting promoters are known in the art and include, but are not limited to, those provided herein (see, e.g., U.S. Pat. No. 7,919,681). Examples of targets include, but are not limited to, the vacuole, endoplasmic reticulum (ER), chloroplast, amyloplast, starch granule, cell wall, seed, or to a particular tissue, e.g., endosperm. Thus, a nucleotide sequence encoding a polypeptide of the invention (e.g., SEQ D NO:1) can be operably linked to a signal sequence for targeting and/or retaining the polypeptide to a compartment within a plant. In some embodiments, the signal sequence may be an N-terminal signal sequence from waxy, an N-terminal signal sequence from gamma-zein, a starch binding domain, or a C-terminal starch binding domain. In further embodiments, the signal sequence can be an ER signal sequence, an ER retention sequence, an ER signal sequence and an additional ER retention sequence. Thus, in some embodiments of the invention, the α-amylase polypeptides can be fused with one or more signal sequences (and/or nucleotide sequences encoding said polypeptides can be operably linked to nucleotide sequences encoding said signal sequences).

As used herein, "expression cassette" means a nucleic acid molecule comprising a nucleotide sequence of interest (e.g., the nucleotide sequence of SEQ ID NO:2, SEQ ID NO:3, SEQ ID NO:4 and/or SEQ ID NO:5), wherein said nucleotide sequence is operatively associated with at least a control sequence (e.g., a promoter). Thus, some embodiments of the invention provide expression cassettes designed to express the nucleotide sequence of SEQ ID NO:2, SEQ ID NO:3, SEQ ID NO:4 and/or SEQ ID NO:5. In this manner, for example, one or more plant promoters operatively associated with the nucleotide sequence of SEQ ID NO:2, SEQ ID NO:3, SEQ ID NO:4 and/or SEQ ID NO:5 or a nucleotide sequence having substantial identity to the nucleotide sequence of SEQ ID NO:2, SEQ ID NO:3, SEQ ID NO:4 and/or SEQ ID NO:5 can be provided in an expression cassette for expression in an organism or cell thereof (e.g., a plant, plant part and/or plant cell).

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event.

In addition to the promoters operatively linked to a nucleotide sequence to be expressed, an expression cassette can also include other regulatory sequences. As used herein, a "regulatory sequence" means a nucleotide sequence located upstream (5' non-coding sequences), within and/or downstream (3' non-coding sequences) of a coding sequence, and/or which influences the transcription, RNA processing or stability, or translation of the associated coding sequence. Regulatory sequences include, but are not limited to, promoters, enhancers, introns, translation leader sequences, termination signals, and polyadenylation signal sequences. In some embodiments, an expression cassette can also include nucleotide sequences encoding signal sequences operably linked to a polynucleotide sequence of the invention.

For purposes of the invention, the regulatory sequences or regions can be native/analogous to the plant, plant part and/or plant cell and/or the regulatory sequences can be native/analogous to the other regulatory sequences. Alternatively, the regulatory sequences may be heterologous to the plant (and/or plant part and/or plant cell) and/or to each other (i.e., the regulatory sequences). Thus, for example, a promoter can be heterologous when it is operatively linked to a polynucleotide from a species different from the species from which the polynucleotide was derived. Alternatively, a promoter can also be heterologous to a selected nucleotide sequence if the promoter is from the same/analogous species from which the polynucleotide is derived, but one or both (i.e., promoter and/or polynucleotide) are substantially modified from their original form and/or genomic locus, and/or the promoter is not the native promoter for the operably linked polynucleotide.

A number of non-translated leader sequences derived from viruses are known to enhance gene expression. Specifically, leader sequences from Tobacco Mosaic Virus (TMV, the "ω-sequence"), Maize Chlorotic Mottle Virus (MCMV) and Alfalfa Mosaic Virus (AMV) have been shown to be effective in enhancing expression (Gallie et al. (1987) *Nucleic Acids Res.* 15:8693-8711; and Skuzeski et al. (1990) *Plant Mol. Biol.* 15:65-79). Other leader sequences known in the art include, but are not limited to, picornavirus leaders such as an encephalomyocarditis (EMCV) 5' non-coding region leader (Elroy-Stein et al. (1989) *Proc. Natl. Acad. Sci. USA* 86:6126-6130); potyvirus leaders such as a Tobacco Etch Virus (TEV) leader (Allison et al. (1986) *Virology* 154:9-20); Maize Dwarf Mosaic Virus (MDMV) leader (Allison et al. (1986), supra); human immunoglobulin heavy-chain binding protein (BiP) leader (Macejak & Samow (1991) *Nature* 353:90-94); untranslated leader from the coat protein mRNA of AMV (AMV RNA 4; Jobling & Gehrke (1987) *Nature* 325:622-625); tobacco mosaic TMV leader (Gallie et al. (1989) *Molecular Biology of RNA* 237-256); and MCMV leader (Lommel et al. (1991) *Virology* 81:382-385). See also, Della-Cioppa et al. (1987) *Plant Physiol.* 84:965-968.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used.

An expression cassette of the invention also can include a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in an expression cassette of the invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac," pp. 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin, which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression cassette of the invention.

In other aspects of the invention a method of increasing the growth rate (weight gain) or the average daily weight gain of an animal is provided, the method comprising feeding to said animal an animal feed composition of the present invention, wherein the growth rate of the animal or the average daily weight gain of the animal is increased by about 0.05 lb/day to about 10 lbs/day as compared to the growth rate of a control animal that is not provided the animal feed composition of the invention. Thus, in some embodiments the increase in growth rate or average daily weight gain can be about 0.05, 0.06, 0.07, 0.08, 0.09, 0.1, 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.25, 1.5, 1.75, 2, 2.25, 2.5, 2.75, 3, 3.25, 3.5, 3.75, 4, 4.1, 4.2, 4.21, 4.22, 4.23, 4.24, 4.25, 4.26, 4.27, 4.28, 4.29, 4.3, 4.31, 4.32, 4.33, 4.34, 4.35, 4.36, 4.37, 4.38, 4.39, 4.4, 4.41, 4.42, 4.43, 4.44, 4.45, 4.46, 4.47, 4.48, 4.49, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, 10 lbs/day, and the like and/or any range therein. In some particular embodiments, the increase in growth rate or average daily weight gain can be from about 0.05 lb/day to about 0.5 lb/per day. In further embodiments, the increase in growth rate or average daily weight gain can be about 0.1 lb/day as compared to the growth of a control animal that is not provided said animal feed composition.

In still further aspects of the invention, a method for reducing the number of days needed to achieve a desired weight in an animal is provided, the method comprising feeding to said animal an animal feed composition of the invention, thereby reducing the number of days needed to achieve a desired weight as compared to the number of days needed to achieve the same desired weight in a control animal that is not fed said animal feed composition.

As used herein, a "desired weight" "or desired finished weight" can mean a live weight or a hot carcass weight. Thus, for example, for cattle, a desired live weight can be between about 950 to about 1,600 lbs and a desired hot carcass weight can be between about 700 to about 1,000 lbs.

Prior to entering a feedlot, cattle spend most of their life grazing on range or pasture land and then are transported to a feedlot for finishing where they are fed grain and other feed concentrates. Generally, cattle enter a feedlot at a weight of about 600 to about 750 lbs. Depending on weight at placement, the feeding conditions, and the desired finished weight, the period in a feedlot can be in a range from about 90 days to about 300 days. The average gain can be from about 2.5 to about 5 pounds per day.

Accordingly, in another aspect of the invention, the number of days needed to achieve a desired weight in an animal fed the animal feed compositions of the invention can be reduced by about 1 day to about 30 days as compared to a control animal that is not fed said animal feed composition. In some embodiments, the number of days needed to achieve a desired weight in an animal fed the animal feed compositions of the invention can be reduced by about 1 day to about 25 days, about 1 day to about 20 days, about 5 days to about 20 days, about 5 days to about 15 days, and the like, as compared to a control animal that is not fed said animal feed composition. Thus, in some embodiments, the number of days needed to achieve a desired weight in an animal fed an animal feed composition of the invention can reduced by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days and the like and/or any range therein.

In other aspects of the invention, a method of increasing the efficiency of feed utilization by an animal is provided, the method comprising feeding to said animal an animal feed composition of the invention in an amount effective to increase the efficiency of feed utilization by said animal as compared to a control animal that is not fed said animal feed composition.

Efficiency of feed utilization can be calculated as the gain in body weight of the animal per the amount of feed provided. In some embodiments, the body weight is the finished body weight prior to slaughter. In further embodiments, the feed provided is the amount of feed that is provided over a period of about 90 days to about 300 days. Thus, in some embodiments the feed provided is the amount of feed that is provided over a period of about 100 days to about 275 days, about 125 days to about 250 days, about 150 days to about 225 days, about 180 days to about 200 days, and the like.

Accordingly, in some embodiments, the time period (number of days) over which the weight gain is measured is 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300 days, and the like, and/or any range therein.

In further aspects of the invention, the feeding value of corn by the animal is increased by about 1% to about 25% as compared to a control animal that is not fed said animal feed composition. The feeding value of corn equals the difference in feed efficiency of the feed composition of the present invention and the feed efficiency of a control animal that is not fed said feed composition, divided by the feed efficiency of said control animal that is not fed said feed composition, all of which is divided by the percent corn inclusion of said feed composition. Accordingly, in some embodiments, the increase in feeding value of corn can be about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, and the like, and/or any range therein. In particular embodiments, the increase in the feed value of corn is about 1% to about 10% as compared to a control. In a representative embodiment, the increase in the feed value is about 5% as compared to a control.

In further aspects of the invention, the efficiency of feed utilization by the animal is increased by about 0.005 to about 0.1 as compared to a control animal that is not fed said animal feed composition. Accordingly, in some embodiments, the increase in efficiency of feed utilization can be about 0.005, 0.006, 0.007, 0.008, 0.009,0.01, 0.011, 0.012, 0.013, 0.014, 0.015, 0.016, 0.017, 0.018, 0.019, 0.02, 0.021, 0.022, 0.023, 0.024, 0.025, 0.026, 0.027, 0.028, 0.029, 0.03, and the like, and/or any range therein. In particular embodiments, the increase in the efficiency of feed utilization is about 0.005 to about 0.01 as compared to a control. In a representative embodiment, the increase in the efficiency of feed utilization is about 0.06 as compared to a control. The efficiency of feed utilization, also known as "G:F", is the average daily gain divided by the dry matter intake per day of the animal.

In some embodiments, the animal is fed about 1 lb to about 30 lbs of an animal feed composition of the invention per animal per day. Accordingly, in some embodiments, the animal is fed about 1 lb, 2 lbs, 3 lbs, 4 lbs, 5 lbs, 6 lbs, 7 lbs, 8 lbs, 9 lbs, 10 lbs, 11 lbs, 12 lbs, 13 lbs, 14 lbs, 15 lbs, 16 lbs, 17 lbs, 18 lbs, 19 lbs, 20 lbs, 21 lbs, 22 lbs, 23 lbs, 24 lbs, 25 lbs, 26 lbs, 27 lbs, 28 lbs, 29 lbs, 30 lbs of the animal feed composition of the invention per animal per day, and the like, and/or any range therein. In some embodiments, the animal is fed about 9 lbs to about 21 lbs of the animal feed composition of the invention per animal per day. In some embodiments, an animal can be fed the animal feed composition of the invention ad libitum, or about one time to about three times per day (e.g., 1, 2, 3) or any combination thereof.

The animal feed composition of the present invention can be fed to any animal, for example, a farm animal, a zoo animal, a laboratory animal and/or a companion animal. In some embodiments, the animal can be, but is not limited to, a bovine (e.g., domestic cattle (cows (e.g., dairy and/or beef)), bison, buffalo), an equine (e.g., horse, donkey, zebra, and the like), an avian (e.g., a chicken, a quail, a turkey, a duck, and the like; e.g., poultry), a sheep, a goat, an antelope, a pig (e.g., swine), a canine, a feline, a rodent (e.g., mouse, rat, guinea pig); a rabbit, a fish, and the like. In some embodiments, the animal can be a cow. In some embodiments the animal can be poultry. In other embodiments, the animal can be a chicken. In further embodiments, the animal can be swine. In still further embodiments, the animal can be a pig.

In further embodiments, the present invention provides a method for increasing the volume of milk produced by a dairy animal (e.g., a cow, a goat, and the like), comprising feeding to said dairy animal an animal feed composition of the present invention, wherein the volume of milk produced by said animal is increased by about 5% to about 200% as compared to the volume of milk produced by a control animal that is not provided said animal feed composition of the invention. In some embodiments, the increase in the volume of milk is in over a time period from about 1 to about 72 hours. In other embodiments, the volume of milk produced by said animal is increased by about 25% to about 175%, about 50% to about 150%, and the like. In further embodiments, the volume of milk produced by said animal is increased by about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195% and/or 200% as compared to a control animal that has not been fed the animal feed composition of the invention.

The terms "increase," "increasing," "increased," "enhance," "enhanced," "enhancing," and "enhancement" (and grammatical variations thereof), as used herein, describe an increase in the average daily weight gain of an animal or the growth rate (weight gain) of an animal by feeding to said animal an animal feed composition of the invention, wherein the average daily weight gain or growth rate of the animal is increased by about 0.05 lbs/day to about 10 lbs/day or an increase in the efficiency of feed utilization by an animal by feeding to said animal the animal feed composition of the invention in an amount effective to increase the efficiency of feed utilization by said animal. This increase in the average daily weight gain, in the growth rate (weight gain), or in the efficiency of feed utilization by an animal can be observed by comparing the average daily weight gain, the growth rate (weight gain) or increase in the efficiency of feed utilization by the animal to an animal not fed an animal feed composition of the invention (i.e., a control).

As used herein, the terms "reduce," "reduced," "reducing," "reduction," "diminish," "suppress," and "decrease" (and grammatical variations thereof), describe, for example, a reduction of or decrease in the number of days needed to achieve a desired weight in an animal as compared to a control (e.g., a control animal that is not fed the animal feed composition).

The present invention is more particularly described in the following examples that are intended as illustrative only since numerous modifications and variations therein will be apparent to those skilled in the art.

EXAMPLES

Experiment 1

Three hundred crossbred steers (Initial BW=658±36 lbs) were utilized in a feedlot finishing trial at the UNL Agricultural Research and Development Center (ARDC) feedlot near Mead, NE. Cattle were limit fed a diet at 2% BW consisting of 32% corn wet distillers grains plus solubles, 32% alfalfa hay, 32% dry-rolled corn, and 4% supplement (DM basis) for five d prior to the start of the experiment. Two-day initial weights were recorded on d 0 and 1 which were averaged and used as the initial BW. The steers were blocked by BW into light, medium, and heavy BW blocks (n=3, 2, and 1 pen replicates, respectively), stratified by BW and assigned randomly to one of 30 pens with pens assigned randomly to one of five dietary treatments. There were 10 head/pen and 6 replications/treatment. Dietary treatments included 1) commercial corn source (CON), 2) Enogen test corn (SYN), 3) 50:50 blend of CON and SYN, 4) CON with wet corn gluten feed (CON-SB), and 5) SYN with wet corn gluten feed (SYN-SB) in a randomized block design (Table 1). Steers were adapted to the finishing diets over a 21-d period with corn replacing alfalfa hay, while inclusion of corn silage, corn wet distillers grain plus solubles (WDGS), and supplement remained the same in all diets. In diets containing wet corn gluten feed (Sweet Bran® (Cargill); SB) the concentration remained the same in all grain adaptation diets. Diets were formulated to meet or exceed NRC requirements for protein and minerals. The final finishing diets provided 360 mg/steer daily of Rumensin (30 g/ton of DM), and 90 mg/steer daily of Tylan (9 g/ton of DM). Steers were implanted on d 1 with Revalor-XS.

All steers were harvested at a commercial abattoir (Greater Omaha Pack, Omaha, NE) on d 173. Final live BW was collected on the d of slaughter and a 4% pencil shrink was applied for calculation of dressing percentage. Feed offered on d 173 was 50% of the previous day DMI and weighed at 4:00 pm. Steers were then shipped and held until slaughter the next day. Hot carcass weight and livers scores were recorded on the d of slaughter. Fat thickness, LM area, and USDA marbling score were recorded after a 48-h chill. Final BW, ADG, and F:G were calculated using HCW adjusted to a common 63% dressing percentage.

Experiment 2

Two hundred-forty crossbred steers (Initial BW=634±34 lbs) were utilized in a feedlot finishing trial at the UNL Panhandle Research and Extension Center (PHREC) feedlot near Scottsbluff, NE. Cattle limit feeding and initial BW protocols were the same as Exp 1. The steers were blocked by BW into light, medium, and heavy BW blocks, stratified by BW and assigned randomly to one of 24 pens with pens assigned randomly to one of four dietary treatments. There were 10 head per pen and 6 replications per treatment. Dietary treatments included 1) CON, 2) SYN, 3) BLEND, and 4) CON with enzyme (Amaize; Alltech, Inc.) added to the diet at a rate of 5g/steer daily (NZ; Table 2). Limit feeding, weighing, blocking, implanting, and grain adaptation procedures were the same as Exp 1. Steers in the heavy, middle, and light BW blocks were harvested at a commercial abattoir (Cargill Meat Solutions, Fort Morgan, CO) on days 148, 169 and 181 (respectively). On the final day steers were withheld from feed and weighed at 8:00 am before being shipped and slaughtered on the same day. Data were analyzed as a randomized block design with initial BW block as a fixed effect and pen as the experimental unit.

TABLE 1

Dietary treatments evaluating test corn and conventional corn with or without Sweet Bran (Exp 1).

| | CON | SYN | BLEND | CON-CGF[1] | SYN-CGF[2] |
|---|---|---|---|---|---|
| Ingredient, % DM | | | | | |
| Commercial Corn | 68.0 | — | 34.0 | 58.0 | — |
| Test corn[3] | — | 68.0 | 34.0 | — | 58.0 |
| Sweet Bran | — | — | — | 25.0 | 25.0 |
| MDGS[4] | 15.0 | 15.0 | 15.0 | — | — |
| Corn silage | 12.0 | 12.0 | 12.0 | 12.0 | 12.0 |
| Meal supplement[5] | 5.0 | 5.0 | 5.0 | 5.0 | 5.0 |
| Fine ground corn | 2.174 | 2.174 | 2.174 | 2.435 | 2.435 |
| Limestone | 1.6 | 1.6 | 1.6 | 1.6 | 1.6 |
| Urea | 0.6 | 0.6 | 0.6 | 0.4 | 0.4 |
| Salt | 0.3 | 0.3 | 0.3 | 0.3 | 0.3 |
| Tallow | 0.125 | 0.125 | 0.125 | 0.125 | 0.125 |
| Trace mineral premix | 0.05 | 0.05 | 0.05 | 0.05 | 0.05 |
| Potassium chloride | 0.02 | 0.02 | 0.02 | — | — |
| Rumensin-90 | 0.0165 | 0.0165 | 0.0165 | 0.0165 | 0.0165 |
| Vitamin ADE premix | 0.015 | 0.015 | 0.015 | 0.015 | 0.015 |
| Tylan-40 | 0.01 | 0.01 | 0.01 | 0.01 | 0.01 |
| Analyzed Nutrient Composition, % | | | | | |
| Starch | 52.48 | 52.55 | 52.52 | 47.75 | 47.81 |
| CP | 12.84 | 12.91 | 12.88 | 12.58 | 12.64 |
| Fat | 4.07 | 4.01 | 4.04 | 3.19 | 3.13 |
| NDF | 15.91 | 15.16 | 15.54 | 18.80 | 18.16 |
| S | 0.16 | 0.15 | 0.15 | 0.19 | 0.18 |
| P | 0.40 | 0.39 | 0.39 | 0.46 | 0.44 |
| K | 0.57 | 0.58 | 0.57 | 0.67 | 0.68 |
| Mg | 0.17 | 0.17 | 0.17 | 0.19 | 0.19 |

[1]Conventional corn with wet corn gluten feed, Sweet Bran

[2]Syngenta test corn with wet corn gluten feed, Sweet Bran

[3]Test corn provided by Syngenta under identity-preserved procedures. Stored, processed, and fed separately

[4]MDGS = modified distillers grains with solubles

[5]Supplement included 30 g/ton Rumensin and 9 g/ton Tylan.

TABLE 2

Dietary treatments evaluating test corn and conventional corn with or without added enzyme (Exp 2).

| | CON | SYN | BLEND | CON-NZ |
|---|---|---|---|---|
| Ingredient | | | | |
| Corn | 64.0 | — | 32.0 | 64.0 |
| Test corn | — | 64.0 | 32.0 | — |
| WDGS | 15.0 | 15.0 | 15.0 | 15.0 |
| Corn silage | 15.0 | 15.0 | 15.0 | 15.0 |
| Liquid Supplement[2,3] | 6.0 | 6.0 | 6.0 | 6.0[4] |
| Analyzed Nutrient Composition, % | | | | |
| Starch | 51.40 | 52.23 | 51.82 | 51.40 |
| CP | 12.96 | 13.41 | 13.18 | 12.96 |
| Fat | 3.44 | 3.89 | 3.67 | 3.44 |
| NDF | 15.46 | 15.66 | 15.56 | 15.46 |
| S | 0.15 | 0.15 | 0.15 | 0.15 |
| P | 0.34 | 0.31 | 0.32 | 0.34 |
| K | 0.54 | 0.52 | 0.53 | 0.54 |
| Mg | 0.15 | 0.15 | 0.15 | 0.15 |

[2]Liquid supplement contained; 0.6% urea, 1.6% Ca, 0.3% salt, 0.02% potassium chloride, vitamins and trace minerals.

[3]Rumensin (30 g/ton) and Tylan (9 g/ton) were added via micromachine.

[4]Enzyme added via micro-machine at the rate of 5 g/steer daily

TABLE 3

Effect of corn hybrid on finishing steer performance and carcass characteristics without Sweet Bran (Exp. 1)

| Item | Dietary Treatments[1] CON | SYN | BLEND |
|---|---|---|---|
| Animal Performance | | | |
| Initial BW, lbs | 672 | 673 | 673 |
| DMI, lbs | 23.0 | 22.4 | 23.0 |
| Final BW, lbs[4] | 1296 | 1291 | 1304 |
| ADG, lbs[4] | 3.61 | 3.57 | 3.64 |
| G:F, lb/lb[4] | 0.159 | 0.161 | 0.159 |
| F:G, lb/lb[4,5] | 6.44 | 6.31 | 6.34 |
| Carcass Characteristics | | | |
| HCW, lbs | 816 | 814 | 821 |
| Dressing % | 62.7 | 62.8 | 62.9 |
| Marbling Score[6] | 461 | 489 | 511 |
| Fat Depth, in | 0.48$^a$ | 0.55$^b$ | 0.57$^b$ |
| LM Area, in$^2$ | 12.9 | 12.5 | 12.3 |
| Calculated Yield Grade[7] | 3.68$^a$ | 3.99$^b$ | 4.10$^b$ |
| Liver Abscesses, % | 8.33 | 5.00 | 5.37 |

[1]CON = control commercial corn hybrid, SYN = Syngenta test corn hybrid, BLEND = 50:50 blend of CON and SYN on a DM basis.

[4]Calculated from HCW adjusted to a common 63% pressing percentage.

[5]Analyzed as G:F, the reciprocal of F:G.

[6]Marbling Score: 300 = Slight$^{00}$, 400 = Small$^{00}$.

[7]Calculated as 2.5 + (2.5 × 12$^{th}$ rib fat) + (0.2 × 2.5 [KPH]) + (0.0038 × HCW) − (0.32 × LM area).

$^{a,b}$Means within a row with unlike superscripts differ ($P < 0.05$).

TABLE 4

Effect of corn hybrid and inclusion of Sweet Bran on finishing steers performance and carcass characteristics (Exp 1)

| | Dietary Treatments[1] | | | |
|---|---|---|---|---|
| | 0% SB | | 25% SB | |
| Item | CON | SYN | CON | SYN |
| Animal Performance | | | | |
| Initial BW, lbs | 671 | 673 | 673 | 674 |
| DMI, lbs | 23.0 | 22.4 | 23.3 | 22.7 |
| Final BW, lbs[3] | 1295 | 1290 | 1278 | 1317 |
| ADG, lbs[3] | 3.60$^{ab}$ | 3.57$^{ab}$ | 3.49$^b$ | 3.72$^a$ |
| G:F[3] | 0.159$^{bc}$ | 0.160$^{ab}$ | 0.151$^c$ | 0.164$^a$ |
| F:G, lb/lb[3,4] | 6.44 | 6.31 | 6.71 | 6.13 |
| Carcass Characteristics | | | | |
| HCW, lbs | 816 | 813 | 805 | 829 |
| Dressing % | 62.7 | 62.8 | 62.8 | 63.1 |
| Marbling Score[5] | 456 | 484 | 443 | 488 |
| Fat Depth, in | 0.48 | 0.56 | 0.48 | 0.53 |
| Ribeye Area, in$^2$ | 12.9 | 12.5 | 12.8 | 13.0 |
| Calculated Yield Grade[6] | 3.67 | 3.98 | 3.67 | 3.83 |
| Liver Abscesses, % | 8.96 | 5.63 | 11.12 | 5.63 |

[1]0% SB = diets without Sweet Bran, 25% SB = diets containing 25% Sweet Bran, CON = commercial corn hybrid, SYN = Syngenta test corn.

[3]Calculated from HCW adjusted to a common 63% dressing percentage.

[4]Analyzed as G:F, the reciprocal of F:G.

[5]Marbling Score: 300 = Slight$^{00}$, 400 = Small$^{00}$.

[6]Calculated as 2.5 + (2.5 × 12$^{th}$ rib fat) + (0.2 × 2.5 [KPH]) + (0.0038 × HCW) − (0.32 × LM area).

$^{a,b,c}$Means within a row with unlike superscripts differ ($P < 0.05$).

TABLE 5

Effect of corn hybrid and inclusion of an alpha amylase enzyme on finishing steer performance and carcass characteristics (Exp 2)

| Item | Dietary Treatment[1] CON | SYN | BLEND | NZ |
|---|---|---|---|---|
| Animal Performance | | | | |
| Initial BW, lbs | 646 | 649 | 647 | 647 |
| DMI, lbs | 23.6 | 23.8 | 23.5 | 23.4 |
| Final BW, lbs[3] | 1257$^a$ | 1301$^b$ | 1299$^b$ | 1299$^b$ |
| ADG, lbs[3] | 3.71$^a$ | 3.94$^b$ | 3.93$^b$ | 3.93$^b$ |
| G:F[3] | 0.158 | 0.165 | 0.166 | 0.167 |
| F:G, lb/lb[3,4] | 6.53 | 6.18 | 6.07 | 6.07 |
| Carcass Characteristics | | | | |
| HCW, lbs | 792$^a$ | 820$^b$ | 818$^b$ | 818$^b$ |
| Dressing % | 62.7 | 63.2 | 63.3 | 63.2 |
| Marbling Score[5] | 451$^a$ | 468$^{ab}$ | 481$^b$ | 468$^{ab}$ |
| Fat Depth, in | 0.57$^a$ | 0.60$^{ab}$ | 0.61$^b$ | 0.60$^{ab}$ |
| Ribeye Area, in$^2$ | 12.1$^a$ | 12.1$^a$ | 12.4$^b$ | 12.4$^b$ |
| Calculated Yield Grade[6] | 3.47 | 3.64 | 3.55 | 3.55 |
| Liver Abscesses, % | 3.33 | 5.00 | 0 | 5.33 |

[1]CON = commercial corn hybrid, SYN = Syngenta test corn, BLEND = 50:50 blend of CON and SYN on a DM basis, NZ = inclusion of a commercially available alpha amylase enzyme in diets based on CON.

[23]Calculated from HCW adjusted to a common 63% pressing percentage.

[4]Analyzed as G:F, the reciprocal of F:G.

[5]Marbling Score: 300 = Slight$^{00}$, 400 = Small$^{00}$.

[6]Calculated as 2.5 + (2.5 × 12$^{th}$ rib fat) + (0.2 × 2.5 [KPH]) + (0.0038 × HCW) − (0.32 × LM area).

$^{a,b}$Means within a row with unlike superscripts differ ($P < 0.05$).

Experiment 3

A 173-d finishing trial was conducted utilizing a number of crossbred steers (initial BW (Body Weight)=685±46 lbs) in a randomized block design. Steers were limit fed a diet at 2% BW consisting of 47.5% alfalfa hay, 47.5% wet corn gluten feed, and 5% supplement (DM (Dry Matter) basis) for five d prior to the initiation of the experiment. Two-day initial weights were recorded on d 0 and 1 and averaged to determine initial BW. Along with measuring initial BW on d 1, steers were implanted with Revalor-XS. The steers were blocked by BW into light and heavy BW blocks stratified by BW and assigned randomly to pen. Pens were then assigned randomly to a dietary treatment with 8 head/pen and 6 replications/treatment.

Dietary treatments (Table 6) were arranged with factors including test corn or control (Enogen or Non-Enogen), and byproduct type (MDGS (Modified Distillers Grains with Solubles) or Sweet Bran). The byproducts utilized in this trial were provided as either a protein source (18% MDGS) or as a means of acidosis control (35% SB (Sweet Bran® (Cargill))). Steers were adapted to the finishing diets over a 21-d period with corn replacing alfalfa hay, while inclusion of sorghum silage, Sweet Bran or MDGS, and supplement remained the same in all diets. Diets were formulated to meet or exceed NRC requirements for protein and minerals. The final finishing diets provided 330 mg/steer daily of Rumensin (30 g/ton of DM), and 90 mg/steer daily of Tylan (8.18 g/ton of DM).

All steers were harvested on d 174 at a commercial abattoir (Greater Omaha Pack, Omaha, NE). Feed offered on d 173 was 50% of the previous day DMI and weighed at 4:00 pm. Steers were then shipped to the commercial abattoir and held until the next day for slaughter. Hot carcass weights and livers scores were recorded on the d of slaughter with carcass characteristics such as12th rib fat thickness, LM area, and USDA marbling score being recorded after a 48-h chill. Yield grade was calculated using the USDA YG equation [YG=2.5+2.5 (fat thickness, in)−0.32 (LM area, $in^2$)+0.2 (KPH fat, %)+0.0038 (HCW, lb)]. Final BW, ADG (Average Daily Gain), and G:F (Gain to Feed ratio) were calculated using HCW (Hot Carcass Weight) adjusted to a common 63% dressing percentage.

TABLE 6

Diet Composition on a DM basis fed to finishing steers

| | Test Corn | | | | Control | | | |
|---|---|---|---|---|---|---|---|---|
| | MDGS[1] | | Sweet Bran | | MDGS[1] | | Sweet Bran | |
| Ingredient, % DM | | | | | | | | |
| Test Corn DRC[2] | 69.5 | — | 52.5 | | — | — | — | |
| Control DRC[2] | — | — | — | — | 69.5 | — | 52.5 | — |
| Sweet Bran | — | — | 35.0 | 35.0 | — | — | 35.0 | 35.0 |
| Modified distillers grains plus solubles | 18.0 | 18.0 | — | — | 18.0 | 18.0 | — | — |
| Sorghum Silage | 7.5 | 7.5 | 7.5 | 7.5 | 7.5 | 7.5 | 7.5 | 7.5 |
| Meal Supplement[4] | 5.0 | 5.0 | 5.0 | 5.0 | 5.0 | 5.0 | 5.0 | 5.0 |
| Fine ground corn | 2.223 | 2.223 | 2.806 | 2.806 | 2.223 | 2.223 | 2.806 | 2.806 |
| Limestone | 1.71 | 1.71 | 1.68 | 1.68 | 1.71 | 1.71 | 1.68 | 1.68 |
| Urea | 0.55 | 0.55 | — | — | 0.55 | 0.55 | — | — |
| Salt | 0.3 | 0.3 | 0.3 | 0.3 | 0.3 | 0.3 | 0.3 | 0.3 |
| Tallow | 0.125 | 0.125 | 0.125 | 0.125 | 0.125 | 0.125 | 0.125 | 0.125 |
| Trace mineral premix | 0.05 | 0.05 | 0.05 | 0.05 | 0.05 | 0.05 | 0.05 | 0.05 |
| Rumensin-90 | 0.0165 | 0.0165 | 0.0165 | 0.0165 | 0.0165 | 0.0165 | 0.0165 | 0.0165 |
| Vitamin ADE premix | 0.015 | 0.015 | 0.015 | 0.015 | 0.015 | 0.015 | 0.015 | 0.015 |
| Tylan-40 | 0.01 | 0.01 | 0.01 | 0.01 | 0.01 | 0.01 | 0.01 | 0.01 |
| Analyzed Nutrient Composition, % | | | | | | | | |
| Starch | 47.56 | 49.08 | 39.06 | 40.21 | 47.14 | 48.74 | 38.74 | 39.95 |
| CP | 12.1 | 12.0 | 13.5 | 13.4 | 12.2 | 12.0 | 13.6 | 13.4 |
| Fat | 4.35 | 4.98 | 3.19 | 3.66 | 4.35 | 5.19 | 3.19 | 3.82 |
| NDF | 15.5 | 14.9 | 20.0 | 19.5 | 16.2 | 15.4 | 20.5 | 19.9 |
| S | 0.22 | 0.22 | 0.21 | 0.16 | 0.22 | 0.21 | 0.21 | 0.21 |
| P | 0.38 | 0.39 | 0.53 | 0.53 | 0.34 | 0.35 | 0.50 | 0.51 |
| K | 0.47 | 0.48 | 0.68 | 0.68 | 0.45 | 0.45 | 0.66 | 0.66 |
| Mg | 0.17 | 0.17 | 0.24 | 0.24 | 0.16 | 0.16 | 0.23 | 0.23 |

[1]MDGS = Modified distillers grains plus solubles
[2]DRC = Dry rolled corn
[4]Supplement included 30 g/ton Rumensin and 9 g/ton Tylan

TABLE 7

Effects of test corn on finishing cattle performance

| | DRC[1] | |
|---|---|---|
| | Test Corn | Control |
| Performance | | |
| Initial BW, lb | 700 | 699 |
| Final BW, lb[5] | 1451[b] | 1433[a] |
| DMI, lb/d | 23.7 | 23.8 |
| ADG, lb[5] | 4.36[b] | 4.25[ab] |
| G:F[5] | 0.184 | 0.178 |
| Carcass Characteristics | | |
| HCW, lb | 912 | 904 |
| Marbling[6] | 505 | 492 |
| LM area, $in^2$ | 14.3 | 14.0 |

TABLE 7-continued

| Effects of test corn on finishing cattle performance | | |
|---|---|---|
| | DRC[1] | |
| | Test Corn | Control |
| Fat Depth, in | 0.55 | 0.59 |
| Cal. YG[7] | 3.24 | 3.41 |

[1]DRC = Dry rolled corn;

[5]Calculated from HCW adjusted to a common 63% dressing percentage

[6]Marbling Score: 400 = Small00; 500 = Modest00

[7]Calculated as 2.5 + (2.5 × $12^{th}$ rib fat) + (0.2 × 2.5 [KPH]) + (0.0038 × HCW) − (0.32 × LM area)

[a,b]Means within a row with unlike superscripts differ ($P < 0.10$).

TABLE 8

| Effects of test corn and byproduct type on finishing cattle performance | | | | |
|---|---|---|---|---|
| | MDGS[1] | | Sweet Bran | |
| | Test Corn | Control | Test Corn | Control |
| Performance | | | | |
| Initial BW, lb | 700 | 698 | 699 | 700 |
| Final BW, lb[5] | 1434 | 1427 | 1447 | 1453 |
| DMI, lb/d | 22.5 | 22.9 | 23.3 | 23.4 |

TABLE 8-continued

| Effects of test corn and byproduct type on finishing cattle performance | | | | |
|---|---|---|---|---|
| | MDGS[1] | | Sweet Bran | |
| | Test Corn | Control | Test Corn | Control |
| ADG, lb[5] | 4.25 | 4.21 | 4.34 | 4.36 |
| G:F[5] | 0.190 | 0.184 | 0.186 | 0.187 |
| Carcass Characteristics | | | | |
| HCW, lb | 903 | 899 | 913 | 916 |
| Marbling[6] | 488 | 494 | 510 | 506 |
| LM area, in[2] | 14.4 | 14.0 | 14.1 | 14.1 |
| Fat Depth, in | 0.56 | 0.59 | 0.59 | 0.58 |
| Cal. YG[7] | 3.21 | 3.43 | 3.42 | 3.40 |

[1]MDGS = Modified distillers grains plus solubles

[5]Calculated from HCW adjusted to a common 63% dressing percentage

[6]Marbling Score: 400 = Small$^{00}$; 500 = Modest$^{00}$

[7]Calculated as 2.5 + (2.5 × $12^{th}$ rib fat) + (0.2 × 2.5 [KPH]) + (0.0038 × HCW) − (0.32 × LM area)

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

That which is claimed is:

1. A method of increasing the efficiency of feed utilization for body weight gain by an animal, the method comprising feeding to said animal an animal feed composition comprising transgenic corn plant material having a recombinant a-amylase comprising an amino acid sequence having at least 95% sequence identity to the amino acid sequence of SEQ ID NO: 1 expressed in the endosperm of seeds or kernels of the transgenic corn plant material, wherein said transgenic corn plant material is fed to the animal in an amount effective to increase the efficiency of feed utilization by said animal as compared with a control animal not fed said transgenic corn plant material;

wherein exogenous alpha-amylase has not been added to the animal feed composition; and wherein the transgenic corn plant material comprises from 25% to 100% by weight of the animal feed composition and increases the efficiency of feed utilization for body weight gain by the animal as compared with the control animal not fed said transgenic corn plant material.

2. The method of claim 1, wherein the efficiency of feed utilization by the animal is increased by about 1% to about 25%.

3. The method of claim 1, wherein the efficiency of feed utilization by the animal as determined by average daily gain divided by the dry matter intake per day of the animal (G:F) is increased by about 0.005 to about 0.03 as compared to a control animal that is not fed said transgenic corn plant material.

4. The method of claim 1, wherein the animal is a mammal, a bird, or a fish.

5. The method of claim 4, wherein the mammal is a bovine, a sheep, a goat, or a pig.

6. The method of claim 1, wherein the recombinant α-amylase is encoded by a nucleotide sequence having at least 95% sequence identity to the nucleotide sequence of SEQ ID NO:2 and/or SEQ ID NO:3.

7. The method of claim 1, wherein the recombinant α-amylase is targeted to an intracellular compartment away from its substrate.

8. The method of claim 7, wherein the recombinant α-amylase is targeted to an organelle selected from the group consisting of chloroplast, vacuole, cytoplasm, apoplast and endoplasmic reticulum.

9. The method of claim 1, wherein the transgenic corn plant material comprises from 30% to 100% by weight of the animal feed composition.

10. The method of claim 1, wherein the transgenic corn plant material comprises from 50% to 100% by weight of the animal feed composition.

11. The method of claim 1, wherein the transgenic corn plant material comprises from 25% to 90% by weight of the animal feed composition.

12. The method of claim 1, wherein the animal is fed from 1 lb to 30 Ibs of the animal feed composition per day.

13. The method of claim 1, wherein the animal is fed from 9 lbs to 21 lbs of the animal feed composition per day.

14. The method of claim 4, wherein the mammal is a domestic cattle.

15. A method of increasing the efficiency of feed utilization for body weight gain by an animal, the method comprising feeding to said animal an animal feed composition comprising transgenic corn plant material from corn event 3272, wherein transgenic corn seeds or kernels from said corn event 3272 express a recombinant α-amylase in the endosperm of the transgenic corn seeds or kernels, and wherein said transgenic corn plant material is fed to the animal in an amount effective to increase the efficiency of feed utilization by said animal as compared with a control animal not fed said transgenic corn plant material;

wherein exogenous alpha-amylase has not been added to the animal feed composition; and wherein the transgenic corn plant material comprises from 25% to 100% by weight of the animal feed composition and increases the efficiency of feed utilization for body weight gain by the animal as compared with the control animal not fed said transgenic corn plant material nor alpha-amylase supplement.

16. The method of claim 15, wherein the efficiency of feed utilization by the animal is increased by about 1% to about 25%.

17. The method of claim 15, wherein the efficiency of feed utilization by the animal as determined by average daily gain divided by the dry matter intake per day of the animal (G:F) is increased by about 0.005 to about 0.03 as compared to a control animal that is not fed said transgenic corn plant material.

18. The method of claim 15, wherein the animal is a mammal, a bird, or a fish.

19. The method of claim 18, wherein the mammal is a bovine, a sheep, a goat, or a pig.

20. The method of claim 18, wherein the mammal is a domestic cattle.

21. The method of claim 15, wherein the transgenic corn plant material comprises from 30% to 100% by weight of the animal feed composition.

22. The method of claim 15, wherein the transgenic corn plant material comprises from 50% to 100% by weight of the animal feed composition.

23. The method of claim 1, wherein the transgenic corn plant material comprises pellets, corn grain, silage, dry-rolled corn kernels, steam flaked corn kernels, whole corn kernels, coarsely cracked corn kernels, or high moisture corn, or any combination thereof.

24. The method of claim 1, wherein the transgenic corn plant material consists of pellets, corn grain, silage, dry-rolled corn kernels, steam flaked corn kernels, whole corn kernels, coarsely cracked corn kernels, or high moisture corn, or any combination thereof.

25. The method of claim 15, wherein the transgenic corn plant material comprises pellets, corn grain, silage, dry-rolled corn kernels, steam flaked corn kernels, whole corn kernels, coarsely cracked corn kernels, or high moisture corn, or any combination thereof.

26. The method of claim 15, wherein the transgenic corn plant material consists of pellets, corn grain, silage, dry-rolled corn kernels, steam flaked corn kernels, whole corn kernels, coarsely cracked corn kernels, or high moisture corn, or any combination thereof.

* * * * *